(12) United States Patent
Bengtsson

(10) Patent No.: US 7,544,185 B2
(45) Date of Patent: Jun. 9, 2009

(54) NEEDLE DEVICE COMPRISING A PLURALITY OF NEEDLES

(75) Inventor: Henrik Bengtsson, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 184 days.

(21) Appl. No.: 10/679,642

(22) Filed: Oct. 6, 2003

(65) Prior Publication Data
US 2004/0162521 A1     Aug. 19, 2004

Related U.S. Application Data

(60) Provisional application No. 60/419,308, filed on Oct. 17, 2002.

(30) Foreign Application Priority Data

Oct. 7, 2002    (DK) ............................... 2002 01494

(51) Int. Cl.
*A61M 5/00* (2006.01)
(52) U.S. Cl. .................................................... 604/173
(58) Field of Classification Search ................ 604/131, 604/136, 157, 181, 173, 182, 185, 187
See application file for complete search history.

(56) References Cited

U.S. PATENT DOCUMENTS

| | | | | |
|---|---|---|---|---|
| 3,572,336 | A | * 3/1971 | Hershberg | 604/136 |
| 4,226,235 | A | 10/1980 | Sarnoff et al. | 128/218 |
| 4,245,634 | A | 1/1981 | Albisser et al. | 128/213 |
| 4,340,048 | A | 7/1982 | Eckenhoff | 128/213 |
| 4,552,561 | A | 11/1985 | Eckenhoff et al. | 604/896 |
| 4,734,092 | A | * 3/1988 | Millerd | 604/67 |
| 5,026,357 | A | 6/1991 | Przuntek et al. | 604/258 |
| 5,390,671 | A | 2/1995 | Lord et al. | 128/635 |

(Continued)

FOREIGN PATENT DOCUMENTS

EP    1 177 802 A1    2/2002

(Continued)

OTHER PUBLICATIONS

Heller Adam, Annual Review Of BioMedical Engineering, (1999), vol. 1, pp. 153-175.

(Continued)

*Primary Examiner*—Kevin C Sirmons
*Assistant Examiner*—Elizabeth R MacNeill
(74) *Attorney, Agent, or Firm*—Marc A. Began

(57) ABSTRACT

A needle device comprises a housing, a base portion having a mounting surface adapted for application to the skin of a patient, and a plurality of needles. Each needle comprises a distal pointed end adapted to penetrate the skin of the subject, and has a first position in which the distal end is retracted relative to the mounting surface, and a second position in which the distal end projects from the mounting surface. The needles are arranged such that at least one needle can be moved from its first to its second position, or vice versa, with at least one other needle not performing the same movement. In this way a plurality of needles can be introduced transcutaneously at a selected site within the body of a subject. The device may comprise a common fluid conduit with at least two of the needles having a proximal opening to be arranged in fluid communication with the common fluid conduit.

23 Claims, 6 Drawing Sheets

U.S. PATENT DOCUMENTS

| | | | | |
|---|---|---|---|---|
| 5,391,950 | A | 2/1995 | Krawczak | 327/384 |
| 5,482,473 | A | 1/1996 | Lord et al. | 439/67 |
| 5,527,288 | A | 6/1996 | Gross et al. | 604/140 |
| 5,568,806 | A | 10/1996 | Cheney et al. | 128/635 |
| 5,858,001 | A | 1/1999 | Tsals et al. | 604/135 |
| 5,931,814 | A | 8/1999 | Alex et al. | 604/131 |
| 5,954,643 | A | 9/1999 | VanAntwerp et al. | 600/316 |
| 5,957,895 | A | 9/1999 | Sage et al. | 604/181 |
| 6,280,148 | B1 | 8/2001 | Zengerle et al. | 417/44.1 |
| 6,540,675 | B2 * | 4/2003 | Aceti et al. | 600/309 |
| 7,004,928 | B2 * | 2/2006 | Aceti et al. | 604/191 |
| 2001/0053887 | A1 | 12/2001 | Douglas et al. | 604/152 |
| 2002/0020646 | A1 * | 2/2002 | Groth et al. | 206/366 |

FOREIGN PATENT DOCUMENTS

| | | | |
|---|---|---|---|
| WO | WO 93/21988 A1 | | 11/1993 |
| WO | 01/93927 | | 12/2001 |
| WO | WO 01/93927 | * | 12/2001 |

OTHER PUBLICATIONS

International Search Report mailed Mar. 15, 2004.

* cited by examiner

B-B

D-D

C-C

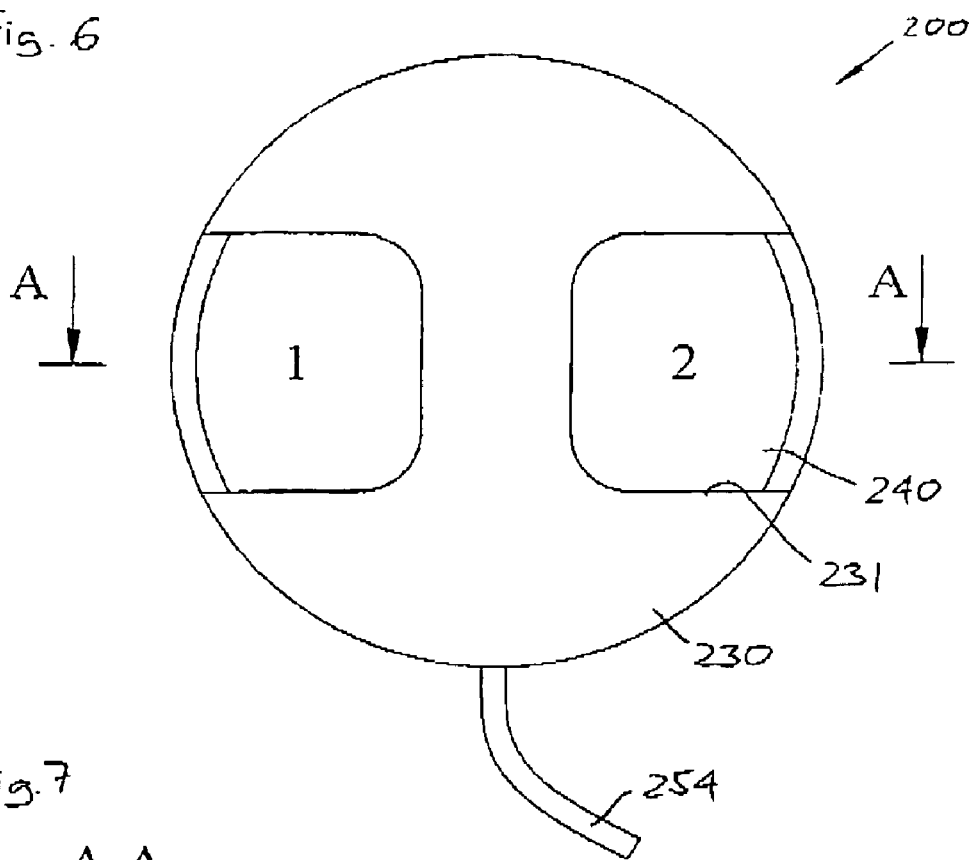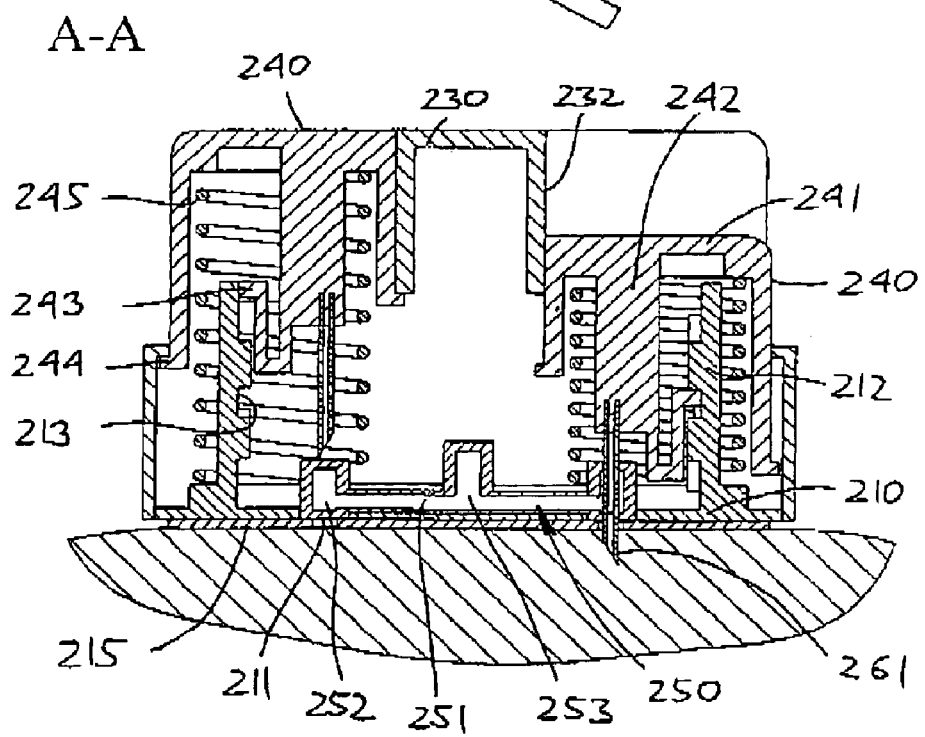

Fig. 10A
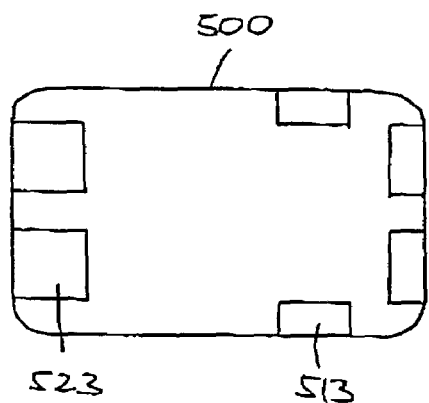
Fig. 10B
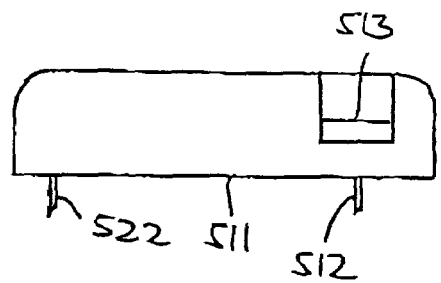
Fig. 9A
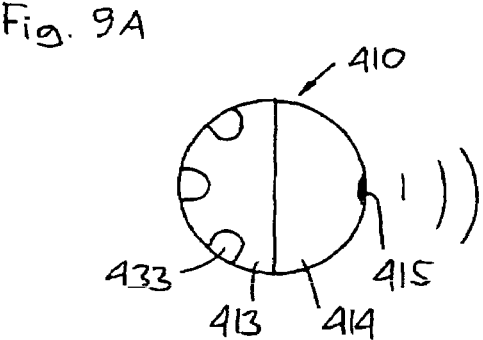
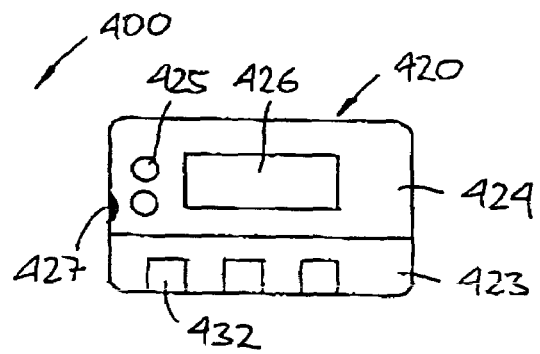
Fig. 9B
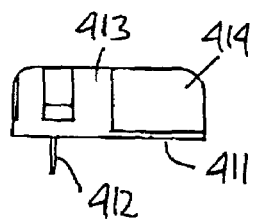
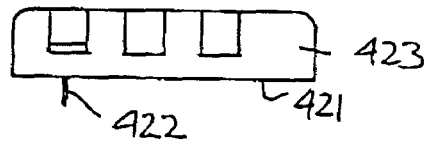

NEEDLE DEVICE COMPRISING A PLURALITY OF NEEDLES

CROSS REFERENCE TO RELATED APPLICATIONS

This application claims priority under 35 U.S.C. 119 of Danish application no. PA 2002 01494 filed Oct. 7, 2002 and U.S. provisional application No. 60/419,308 filed Oct. 17, 2002, the contents of both are fully incorporated herein by reference.

The present invention generally relates to the insertion of needles. More specifically, the invention relates to a needle device for individually introducing a plurality of needles transcutaneously at a selected site within the body of a subject. Especially, the invention relates to insertion of infusion needles for the infusion of a drug, to insertion of needle-formed sensors, as well as to insertion of insertion needles for easy transcutaneous placement of a transcutaneous device such as a sensor.

BACKGROUND OF THE INVENTION

In the disclosure of the present invention reference is mostly made to the treatment of diabetes by injection or infusion of insulin, however, this is only a preferred use of the present invention.

Diabetes mellitus is the common name for at least 2 different diseases, one characterised by immune system mediated specific pancreatic beta cell destruction (insulin dependent diabetes mellitus (IDDM) or type 1 diabetes), and another characterised by decreased insulin sensitivity (insulin resistance) and/or a functional defect in beta cell function (non-insulin dependent diabetes mellitus (NIDDM) or type 2 diabetes).

The principal treatment of type 1 diabetes is straight forward substitution of the missing insulin secretion, whereas treatment of type 2 is more complicated. More specifically, in early stages of type 2 diabetes treatment a number of different types of drugs can be used, e.g. drugs which increase insulin sensitivity (ciglitazones), decrease hepatic glucose output (e.g. metformin), or reduce glucose uptake from the gut (alfa glucosidase inhibitors), as well as drugs which stimulate beta cell activity (e.g. sulfonylurea/meglitinides). However, the above-described deterioration is reflected in the fact that beta cell stimulators will eventually fail to stimulate the cell, and the patient has to be treated with insulin, either as mono therapy, or in combination with oral medication in order to improve glucose control.

Currently, there are two principal modes of daily insulin therapy, the first mode including syringes and insulin injection pens. These devices are simple to use and are relatively low in cost, but they require a needle stick at each injection, typically 3-4 times or more per day. The second mode is infusion pump therapy, which entails the purchase of a relatively expensive pump, for which reason the initial cost of the pump is often a barrier to this type of therapy. Although more complex than syringes and pens, the pump offer the advantages of continuous infusion of insulin, precision in dosing and optionally programmable delivery profiles and user actuated bolus infusions in connections with meals.

Addressing the above problem, several attempts have been made to provide drug infusion devices that are low in cost and convenient to use. Some of these devices are intended to be partially or entirely disposable and may provide many of the advantages associated with an infusion pump without the attendant cost and inconveniencies, e.g. the pump may be prefilled thus avoiding the need for filling or refilling a drug reservoir. To keep costs low, many of the proposed devices operate with fixed insulin flow rates which may meet cost targets but still require bolus injections at mealtimes. Examples of this type of infusion devices are known from U.S. Pat. Nos. 4,340,048 and 4,552,561 (based on osmotic pumps), U.S. Pat. No. 5,858,001 (based on a piston pump), U.S. Pat. No. 6,280,148 (based on a membrane pump), U.S. Pat. No. 5,957,895 (based on a flow restrictor pump (also know as a bleeding hole pump)), or U.S. Pat. No. 5,527,288 (based on a gas generating pump), which all in the last decades have been proposed for use in inexpensive, primarily disposable drug infusion devices, the cited documents being incorporated by reference.

Addressing the need for an inexpensive infusion pump capable of also providing bolus injections at mealtimes, EP 1 177 802 describes a wearable, self-contained drug infusion device comprising a disposable (prefilled) reservoir portion and a durable control portion which in combination with a remote control and programming device may provide most of the features normally associated only with more costly durable pump systems.

For any disposable drug infusion device the costs incurred when using it will be of great importance for the acceptance of the device and thereby the success in the marketplace. Especially, the overall costs for the use of this type of devices will have to be compared with traditional injection therapy or traditional pump treatment.

Although the above-described drug infusion pumps, either disposable or durable, may provide convenience of use and improved treatment control, it has long been an object to provide a drug infusion system for the treatment of e.g. diabetes which would rely on closed loop control, i.e. being more or less fully automatic, such a system being based on the measurement of a value indicative of the condition treated, e.g. the blood glucose level in case of insulin treatment of diabetes. In principle, such systems have been known for more than two decades, see for example U.S. Pat. No. 4,245, 634 which discloses an artificial beta cell for regulating blood glucose concentration in a subject by continuously analyzing blood from the patient and deriving a computer output signal to drive a pump which infuses insulin at a rate corresponding to the signal, however, mainly due to problems associated with the glucose sensors such systems have until today not been very successful. Although a closed loop system would be a desirable implementation of a given sensor system, such a sensor could also be utilized as a monitor system providing the patient with information for manually controlling treatment, e.g. insulin treatment by injections and/or infusion by pump.

A given monitor system for measuring the concentration of a given substance may be based on invasive or non-invasive measuring principles. An example of the latter would be a non-invasive glucose monitor arranged on the skin surface of a patient and using near-IR spectroscopy, however, the present invention is concerned with the introduction of a transcutaneous device such as a sensor element.

In recent years, a variety of electrochemical sensors have been developed for a range of applications, including medical applications for detecting and/or quantifying specific agents in a patient's blood. As one example, glucose sensors have been developed for use in obtaining an indication of blood glucose levels in a diabetic patient. As described above, such readings can be especially useful in monitoring and/or adjusting a treatment regimen which typically includes regular administration of insulin to the patient.

When a sensor element is introduced subcutaneously, the body responds to the element as an insult and produces a specialized biochemical and cellular response which may lead to the development of a foreign body capsule around the implant and consequently may reduce the flux of glucose to the sensor. Consequently, the percutaneous approach aims to acquire data during the first period of this tissue response.

The monitoring method can be of three types: non-reactive, reversibly reactive or irreversibly reactive. The type of sensor which, thus far, has been found to function most effectively in vivo is the amperometric sensor relying on irreversible, transport-dependent reactive glucose assays. For a detailed review of the different types of glucose sensors reference is made to Adam Heller, Implanted electrochemical glucose sensors for the management of diabetes, Annu. Rev. Biomed. Eng. 1999, 01:153-175.

The sensor may be placed subcutaneously being connected to external equipment by wiring or the substance (fluid) to be analysed may be transported to an external sensor element, both arrangements requiring the placement of a subcutaneous component, the present invention addressing both arrangements. However, for simplicity the term "sensor" is used in the following for both types of sensor elements.

Turning to the sensor elements per se, relatively small and flexible electrochemical sensors have been developed for subcutaneous placement of sensor electrodes in direct contact with patient blood or other extra-cellular fluid (see for example U.S. Pat. No. 5,482,473), wherein such sensors can be used to obtain periodic or continuous readings over a period of time. In one form, flexible transcutaneous sensors are constructed in accordance with thin film mask techniques wherein an elongated sensor includes thin film conductive elements encased between flexible insulative layers of polyimide sheet or similar material. Such thin film sensors typically include exposed electrodes at a distal end for transcutaneous placement in direct contact with patient blood or other fluid, and exposed conductive contacts at an externally located proximal end for convenient electrical connection with a suitable monitor device Insertion devices for this type of sensors are described in, among others, U.S. Pat. Nos. 5,390,671, 5,391,950, 5,568, 806 and 5,954,643 which are hereby incorporated by reference.

More specifically, U.S. Pat. No. 5,954,643 discloses an insertion set comprising a mounting base defining an upwardly open channel for receiving and supporting a proximal end of a flexible thin film sensor, the sensor further including a distal segment with sensor electrodes thereon which protrudes from the mounting base for transcutaneous placement, wherein the sensor distal segment is slidably carried by a slotted insertion needle fitted through the assembled base. Placement of the insertion set against the patient's skin causes the insertion needle to pierce the skin to carry the sensor electrodes to the desired subcutaneous site, after which the insertion needle can be slidably withdrawn from the insertion set. The mounting base further includes a fitting and related snap latch members for mated slide-fit releasable coupling of conductive contact pads on a proximal end of the sensor to a cable connector for transmitting sensor signals to a suitable monitoring device.

A similar arrangement is known from U.S. Pat. No. 5,568, 806 disclosing an insertion set comprising an insertion needle extending through a mounting base adapted for mounting onto the patient's skin. A flexible thin film sensor includes a proximal segment carried by the mounting base and adapted for electrical connection to a suitable monitor or the like, and a distal segment protruding from the mounting base with sensor electrodes thereon for transcutaneous placement. The distal segment of the sensor and a distal segment of the insertion needle are positioned within a flexible cannula which extends from the mounting base, whereby placement of the mounting base onto the patient's skin causes the insertion needle to pierce the skin for transcutaneous placement of the cannula with the sensor therein. The insertion needle can then be withdrawn from the cannula and the mounting base to leave the sensor distal segment at the selected insertion position, with the sensor electrodes being exposed to patient blood or other extra cellular fluid via a window formed in the cannula.

Although the above-described insertion sets provide reliable means for introducing a needle formed sensor (i.e. having an oblong, needle-like appearance but not necessarily comprising a pointed distal tip), a number of disadvantages still prevail.

As stated above, the percutaneous approach aims to acquire data during the first period of time after insertion of the device, after which a new sensor is placed at a different place. Although such a short period of time will remove the problems of long-term encapsulating reactions, a tissue response will immediately begin after insertion, the body trying to isolate the implanted object by tissue remodelling. This response may have a profound and varying effect on glucose transport, even over a short period of use, e.g. 1-4 days, this calling for recalibration of the implanted sensor or the introduction of a new electrode.

In addition to the costs associated with replacement of sensor elements, also the replacement as such may be considered cumbersome by the patient, e.g. the old sensor would have to be removed and a new mounted and actuated.

As for the above-described disposable pump devices, the costs incurred when using a sensor system based upon disposable sensor elements will be of great importance for the acceptance of such a system and thereby the success in the marketplace. Especially, the overall costs for the use of this type of system will have to be compared with traditional measuring of values, e.g. blood glucose measuring based on needle puncture.

DISCLOSURE OF THE INVENTION

Having regard to the above-identified problems, it is an object of the present invention to provide systems and devices by which the costs associated with the use of disposable, subcutaneous devices can be lowered allowing more patients to utilize these devices and to thereby improve the quality of treatment. In this context, the term subcutaneous device is used to identify devices which are based on the introduction of a subcutaneous element through the skin of a subject, e.g. an infusion needle or a needle-introduced sensor element.

It is well known that an infusion needle can only remain at a given site for a limited period of time, typically three days, this to avoid ingrowth of bacteria, drug introduced tissue damage as well as inflammatory reactions. The same type of considerations applies in respect of sensor elements.

Consequently, for a given disposable or semi-disposable infusion device, the maximum number of days it can be utilized will be determined by the period of time which the needle can be used, typically three days. Correspondingly, the hitherto proposed devices have mainly been relatively simple providing merely a basal infusion rate, or have been based on systems comprising disposable as well as durable components, this allowing the more complex and costly components to be reused a number of times. However, irrespective of the nature of a given infusion device (simple or complex, disposable or semi-disposable), it would greatly reduce the costs of operation if the operational lifetime for such a device could be prolonged, for example halved if it could be used for six days instead of three days.

Indeed, for traditional durable infusion pumps, which are designed for an operational life of 3-4 years, the above problem has been overcome by utilizing separate needle devices (so-called "infusion sets") which are connected to an outlet opening of the infusion pump by a flexible catheter tubing.

Although it in principle would be possible to utilize a given disposable infusion device in combination with a number of such infusion sets to thereby extend the operational lifetime, this "in-between" solution is by most people not considered attractive as it would "dilute" the advantages associated with a disposable drug infusion device. More specifically, most of the hitherto proposed disposable drug infusion devices have been designed as easy-to-use "place-and-forget" devices comprising a lower adhesive surface adapted to be mounted on a skin surface of a user. The infusion needle may be mounted protruding from the lower surface such that it is inserted as the device is mounted on the skin, or the needle may be provided in a retracted position for introduction into the skin after placement, this allowing the needle to be fully disguised from the view of the user.

Just as for a disposable pump device, it would also be desirable to lower the costs for a skin-mounted sensor device by extending the operational lifetime therefore, especially if the two types of devices were integrated into a single, self-contained device.

Accordingly, in a first aspect of the invention a needle device is provided which comprises a housing, a base portion having a mounting surface adapted for application to the skin of a subject (patient or user), adhesive means arranged on the mounting surface for adhering the needle device to the skin of the subject, a plurality of needles, each needle comprising a distal pointed end adapted to penetrate the skin of the subject, wherein each needle has a first position in which the distal end is retracted relative to the mounting surface, and a second position in which the distal end projects from the mounting surface. The needles are arranged such that at least one needle can be moved from its first to its second position or from its second to its first position with at least one other needle not performing the same movement.

In other words, at least one movement of one needle can be performed without another needle performing the same movement. In accordance with the nature of an actual needle device and the nature of the individual needles, this arrangement can be used to perform a number of needle "actions".

In the present context the term "needle" is used to denote any structure having an oblong, needle-like appearance, e.g. infusion needle, needle sensor or insertion needle. The length of the projecting portion of such a needle and thereby the depth of penetration may be from 0.5 to about 8 mm, preferably about 3-5 mm. In the context of the present application the term "needle" also encompasses an array of micro needles, i.e. a plurality of very short needles mounted together and acting as a single "needle means".

In exemplary embodiments, the skin-contacting mounting surface is provided with a pressure-sensitive adhesive which allows the device to be affixed to the skin of the subject user. To prevent access to the needles in their retracted position, the base portion may comprise a plurality of needle apertures through which the individual needles are moved. Advantageously a removable release liner is provided for covering the adhesive and the needle apertures.

One or more of the needles may be individually operatable between their respective first and second positions, just as some or all of these needles may be individually operatable between their respective second and first positions. By the term "individually operatable" is meant that the operation of a given needle between its two positions does not influence the operation of other needles.

Some of the needles may be functionally coupled such that their movement is restricted or coupled relative to other needles. For example, for a given type or class of needles (e.g. hollow infusion needles or sensor needles) the needles may be arranged such that only one needle of a given type can be positioned in the second position at a given time, e.g. to introduce a second needle the first needle will have to be retracted, or the introduction of the second needle will automatically withdraw the first needle to its second position. In exemplary embodiments all the needles are of the same type.

Thus, in exemplary embodiments the needle device comprises needle actuating means associated with a plurality of the needles (but not necessarily all of the needles), the needle actuating means being operatable between a first actuating position and a second actuating position, whereby a first associated needle is moved from its first to its second position (i.e. introduced) and a second associated needle is moved from its second to its first position (i.e. retracted). The needle actuating means may be operatable between a plurality of actuating positions, each actuating position being associated with a corresponding needle. As follows from this, each time the actuating means is operated between two actuating positions, a needle is introduced and the previously introduced needle is retracted into the device.

As many people dislike needles, or even are afraid therefore, it would be advantageously if the device can be supplied to the user with all needles in their retracted positions (and thereby out of sight), this allowing the device to mounted on the skin of the user (e.g. by means of an adhesive skin-contacting surface) without at the same time having to introduce a needle. Thus, in exemplary embodiments the needle actuating means is operatable between an initial position, in which all associated needles are in their first position, and an actuating position, whereby a (first) needle is moved from its first to its second position.

Correspondingly, to retract all needles before the device is removed from the skin of the user, the needle actuating means is advantageously operatable between an actuating position, in which an associated (last) needle is in its second position, and an end position in which all associated needles are in their first position. In order to allow the device to be removed at any given time (i.e. before the last needle has been used), it may be desirable to allow any projecting needle to be retraced independently of the actuating means, however, as this situation of use is not considered to be "normal", it would for most practical purposes be acceptable to dispense with such a feature, such that the device is simply pulled off the skin with a projecting needle. After this, it would then be possible to "dial" the device through all actuating positions to the end position.

As some people dislike the situation in which they have to "actively" introduce the needle (i.e. when the movement of the needle is directly linked to the actuating operation performed by the user), one or more of the needles may be associated with actuation means comprising a first biasing means and being operatable between an initial position and an actuating position, whereby the needle is released from its first to its second position by a force generated by the first biasing means. Correspondingly, to pull out a given needle, the actuation means may comprise a second biasing means and be operatable between the actuating position and an end position, whereby the needle is pulled from its second to its first position by a force generated by the second biasing means.

The above described embodiments have all been intended for manual operation, however, in exemplary embodiments the needles (either directly or via the above-described actuating means) may be operated by electronically controllable driving means for operating a needle or the actuating means between at least two actuating positions. In this way the user does not have to remember to introduce a new needle, e.g. every third day. In case the needles have to be shifted manually, an integrated communication means (e.g. audible alarm or visual display) may be used to remind the user that the needle has to be exchanged.

To prevent reuse of a given needle, means preventing a needle from being moved from its first to its second position more than once is advantageously provided.

In the above disclosure of the invention, embodiments for a "general" multi-needle device has been described, however, the needle device may be specifically adapted for a number of different purposes.

Thus, in a second aspect the needle device as described above comprises a common fluid conduit means, wherein at least two of the needles are hollow having a distal and a (more) proximal opening, the proximal opening being in fluid communication with the common fluid conduit means when the needle is in its second position. The distal opening may be arranged corresponding to the distal pointed end of the needle, however, one or more distal openings may be arranged proximally of the distal end, e.g. in case the needle has a closed conical end portion. In exemplary embodiments, the proximal opening of a given hollow needle is not in fluid communication with the common fluid conduit means when the needle is in its first position, i.e. only a projecting hollow needle is in fluid communication with the common fluid conduit means. The common fluid conduit means may have any configuration such as tubing, a channel or an opening. In this way the needle device can be used in combination with other devices when the common fluid conduit means is provided with a fluid inlet port (e.g. a traditional durable infusion pump) or it may be integrated into a given device.

In an exemplary embodiment the needle device is associated with a reservoir adapted to contain a liquid drug and comprising an outlet in fluid communication with the common fluid conduit means. In this configuration a combined reservoir and needle device is formed in which the reservoir may be fillable or prefilled. Such a device may be adapted for cooperation with means for expelling drug from the reservoir, however, advantageously the combined device further comprises expelling means for expelling a drug out of the reservoir and through the skin of the subject via the common fluid conduit means and a hollow needle. The expelling means may be in the form of any of the above-described pumps.

As appears, in the latter configuration a self-contained drug infusion pump is provided comprising a plurality of infusion needles thereby providing extended operational life for the (disposable) pump device. For example, by providing 4 needles each intended for 3 days use, a disposable device can be used for 12 instead of 3 days thereby dramatically reducing the costs of operation. Indeed, in this situation it would also be feasible to provide enhanced functionality as the costs will be distributed over an extended period of time. The number of needles which can be used will to a certain degree depend on the actual physical size of the device, as the needles preferably should be introduced with a given minimum distance between each other.

In a third aspect the needle device of the invention comprises at least one needle in the form of a needle sensor comprising sensor means capable of being influenced by a body substance and producing a signal corresponding to a parameter thereof, e.g. the blood glucose concentration. A given needle sensor may comprise a pointed distal end and have a rigidity allowing it to be introduced without the aid of an insertion needle as a "general" needle as described above, however, it may be desirable to provide an insertion needle adapted to cooperate with the needle sensor for inserting the needle sensor subcutaneously. In this case the needle sensor may have a blunt distal end, the insertion needle comprising a pointed distal end in accordance with the invention.

Thus, in a further embodiment at least one of the needles is in the form of an insertion needle for inserting a transcutaneous device, e.g. a needle formed sensor. The insertion needle may have any desirable configuration such as solid or grooved. The signal from the sensor element is conducted through the needle sensor to a control means adapted to receive the signals from the sensor element and generate signals in response thereto providing an indication of the desired body substance parameter, e.g. the glucose level which may be indicated on an associated display. The control means may be formed integrally with the needle device or the signals may be transmitted to an external control unit. In contrast to an infusion needle, an insertion needle will have to be withdrawn after the sensor has been placed transcutaneously, either into the device or fully removed therefrom. The same apply to the individual sensors, which after used should be withdrawn.

The sensor means may be also be arranged within the device and be adapted to draw a body substance through a hollow needle, the sensor producing a signal corresponding to a parameter of the body substance, e.g. the blood glucose concentration.

As appears, by providing a sensor device comprising a plurality of (needle-) insertable sensor means, the operational life can be extended. For example, by providing 4 sensors each intended for 3 days use, a disposable device can be used for 12 instead of 3 days thereby dramatically reducing the costs of operation. Indeed, in this situation it would also be feasible to provide enhanced functionality as the costs will be distributed over an extended period of time. As for the infusion pump, the number of sensors which can be used will to a certain degree depend on the actual physical size of the device, as the sensors preferably should be introduced with a given minimum distance between each other.

In an exemplary embodiment of the invention, a system is provided comprising a sensor portion having a plurality of individually insertable sensors, as well as a drug infusion portion comprising a plurality of individually insertable infusion needles.

The system may be in the form of a closed loop system adapted for controlling the blood glucose concentration in the body of a patient, comprising sensor means having a sensor system adapted for providing a sensor signal indicative of a glucose level in blood, the sensor system comprising a sensor element, control means adapted to receive the signals from the sensor system and generate command signals in response thereto in order to keep the blood glucose level of the patient within a desired range, and delivery means for delivering an amount of at least one drug having a blood glucose regulating effect, wherein operation of the delivery means is affected by the command signals.

In a broader aspect, a value indicative of a level of a body fluid parameter is determined, and an effective amount of a drug having a regulating effect on that body fluid parameter is infused into the patient in response to the determined value in order to keep the body fluid parameter level of the patient within a desired range.

The system may be provided as one or more individual units. In an exemplary embodiment a single, self-contained combined sensor and prefilled pump is provided adapted to be mounted on a skin-surface of a user. In a further exemplary embodiment of the system, an individual sensor assembly and an individual drug infusion pump assembly is provided. The two assemblies may be adapted to be locked to each other and utilized as a single unit, or the two assemblies may be mounted on the skin of the user independently but in communication with each, e.g. by cordless communication means. When the system is provided in the form of separate sensor and pump assemblies, it would be possible to offer different types of sensor assemblies and different types of pump assemblies.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject.

BRIEF DESCRIPTION OF THE DRAWINGS

In the following the invention will be further described with references to the drawings, wherein FIG. 6 shows a further needle device seen from above, FIG. 7 shows a sectional view of the needle device of FIG. 6 along the line A-A, FIGS. 9A and 9B show an upper respectively a side view of a system comprising sensor device and an insulin delivery device, and FIGS. 10A and 10B show an upper respectively a side view of a device comprising sensor and delivery means.

DESCRIPTION OF EXEMPLARY EMBODIMENTS

Figure 1:
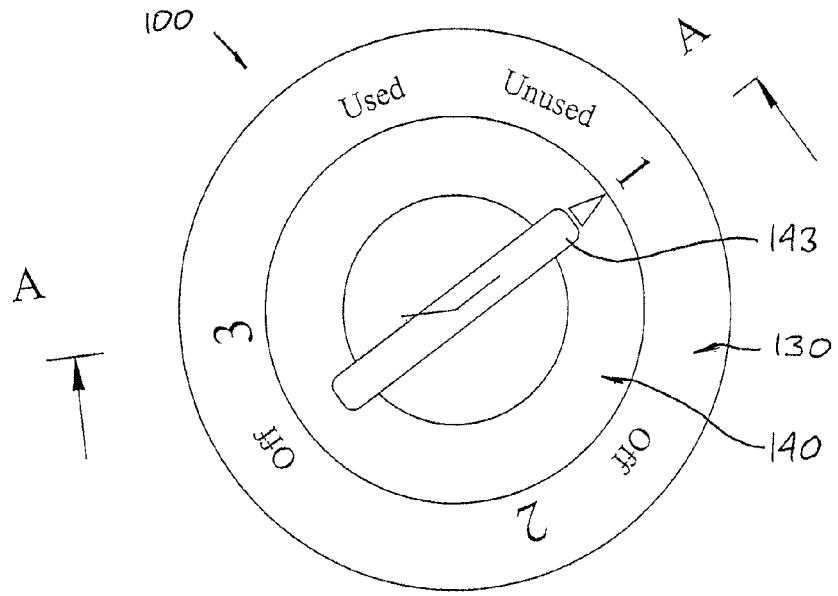
FIG. 1 shows a needle device seen from above.

When in the following terms as "upper", "lower", "right" and "left" or similar relative expressions are used, these only refer to the appended figures and not to an actual situation of use. Further, the term "trace" is used to describe an "open" structure formed in a surface, e.g. a groove, whereas the term "channel" is used to describe a "closed" tubular structure which may have any cross-sectional configuration.

With reference to FIGS. 1-5 a first embodiment of a needle device will be described. It is to be noted that in FIGS. 3 and 5 the sectional views correspond to the full device and not the sectional device of FIG. 2. More specifically, the needle device 100 comprises a base plate member 110, a core member 120 connected to the base plate member, a housing member 130 also connected to the base plate member, and a moveable control member 140, the members in combination forming a device having a generally cylindrical configuration.

The base plate member comprises a lower surface with adhesive means 115 adapted for releasable application to the skin of a subject, an upper surface, and three openings 111. The core member is in the form of a downwardly open hollow cylindrical body having a cylindrical wall 121 with an inner and an outer surface and in the vicinity of the lower free edge an outwardly projecting rim 122, and an upper wall 123 having two circumferentially arranged stepped portions. The core member is connected to the upper surface of the base plate member providing a generally closed space suitable for accommodating drug delivery means, e.g. a reservoir and expelling means. The housing member is in the form of a hollow cylindrical body having a cylindrical wall 131 with an inner and an outer surface, and an upper circumferential flange portion 132 with a free inner edge. The housing member is connected to the base plate member at the periphery thereof. The control member is in the form of a downwardly open hollow cylindrical body having a cylindrical wall 141 with an inner and an outer surface, and an upper wall 142 on the upper surface of which is arranged a gripping member 143. The control member is arranged around the core member with the inner respectively the outer cylindrical wall surfaces in rotational engagement with each other. At the lower end the control member engages the outwardly projecting rim 122 of the core member, and at the upper end it engages the inner free edge of the upper circumferential flange portion 132 and, in part, the upper wall 123 of the core member, whereby the control member is prevented from moving axially.

Between the upper surface of the base plate member and the core member a common conduit member 150 is interposed, comprising three hollow arms 151 projecting through the rim 122 of the core member, each arm having a peripheral needle-penetratable, self-sealing closed end portion 152 in fluid communication with an axially arranged hub portion 153 serving as a common fluid inlet means.

Figure 2:
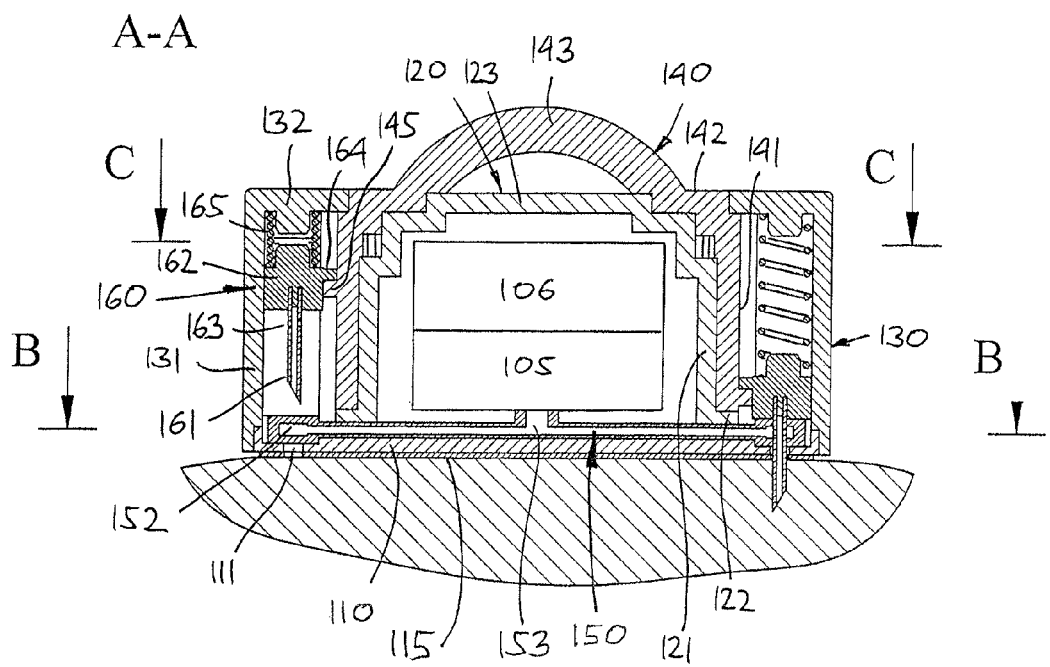
FIG. 2 shows a sectional view of the needle device of FIG. 1 along the line A-A.
Figure 3:
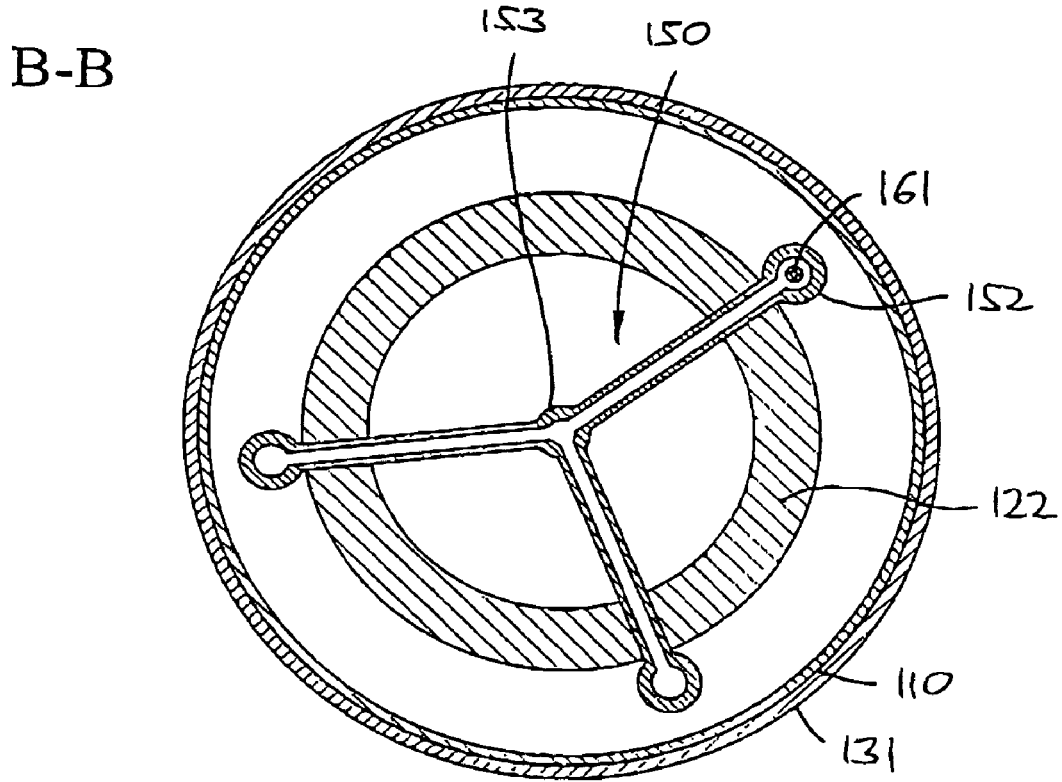
FIG. 3 shows a sectional view of the needle device of FIG. 2 along the line B-B.

As appears from FIG. 2, a circumferential space is provided between the control member and the housing member, in which space three needle assemblies are arranged and allowed to move in a controlled manner, as well as the end portions of the common conduit member.

Each needle assembly 160 comprises a needle device 161 (or just needle) having a distal pointed end adapted to penetrate the skin of the subject, and a proximal end mounted in a needle carrier 162, each needle being arranged in register with a corresponding opening in the base plate member. In the shown embodiment the needle is in the form of a hollow infusion needle having an open distal end and a closed proximal end as well as a pair of opposed side openings 163 allowing the interior of the needle to communicate with an exterior space. The needle carrier comprises a body with a projecting steering pin 164. Each needle carrier is guided in a guide structure 133 associated with the inner surface of the housing member, the guide structure being arranged in register with the respective end portions of the common conduit member. In the shown embodiment the guide structure comprises a pair of opposed walls projecting from the inner surface of the housing member. On the outer surface of the control member a circumferentially projecting steering guide 145 is arranged having an upwardly facing guide surface 146, 147, 148. In the shown embodiment the guide surface may be considered a non-continuous cam surface.

Figure 5:
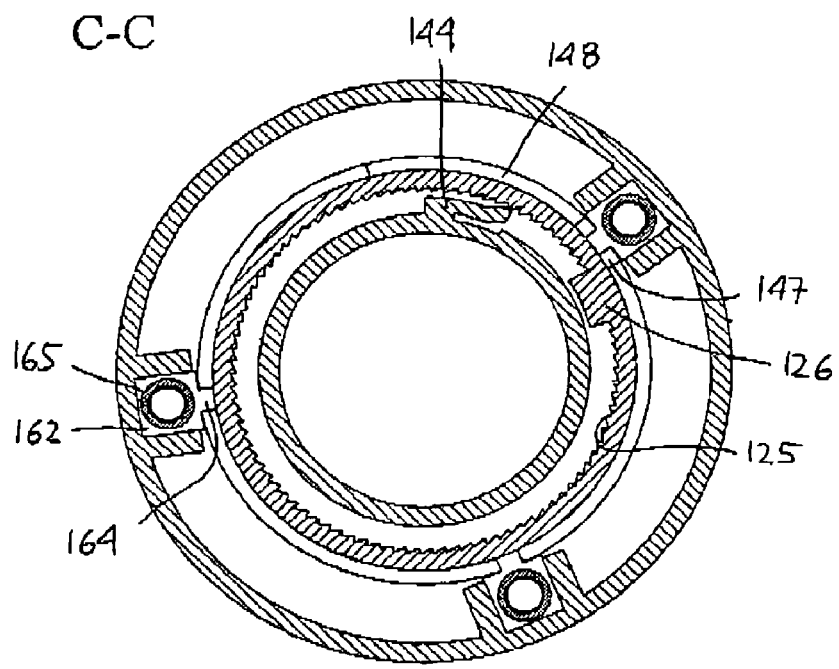
FIG. 5 shows a sectional view of the needle device of FIG. 2 along the line C-C.

As appears from FIGS. 2 and 5, each needle carrier is guided in combination by the guide structure of the housing member and the outer wall surface of the control member, with the lower surface of the steering pin being supported on the upper surface of the steering guide. Between the upper surface of the carrier member and the lover surface of the upper circumferential flange portion 132 a biasing member 165 is arranged providing a downwardly directed force on the carrier member. In the shown embodiment the biasing member is in the form of a helical spring held in place by projections formed on the carrier member respectively the flange portion, however, the biasing means could also be in the form of a leaf spring, a compressible foam member, a gas spring or any other suitable spring means (this also applies to the biasing means of the second embodiment).

By this arrangement the needle assemblies are only allowed to move perpendicular relative to the general "horizontal" plane of the base plate member, the "vertical" position being determined by the configuration of the guide surface 146 and the position thereof relative to the needle assemblies.

Figure 4:
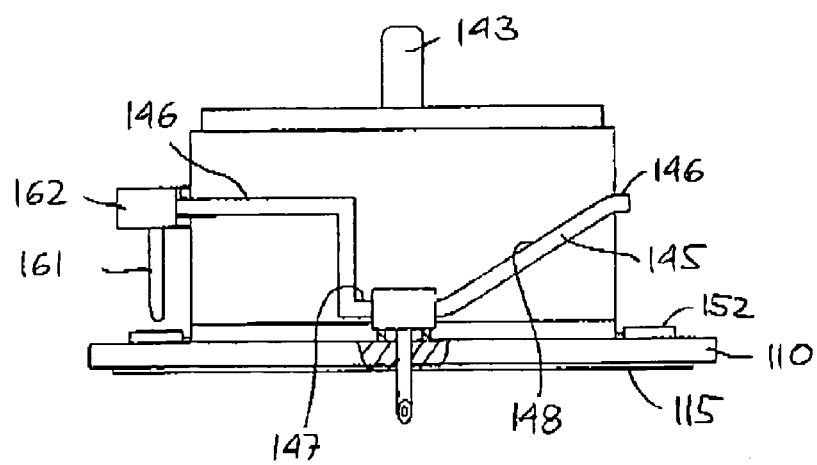
FIG. 4 shows a side view of the needle device of FIG. 1 with the housing member removed.

Turning to FIG. 4 the configuration and the function of the guide surface will be described. The shown guide surface comprises three portions, a first "upper" horizontal portion spanning approximately 300 degrees of the circumference of the control member and supporting the needle assemblies in a first position in which the distal end is retracted relative to the mounting surface, a second portion 147 supporting a needle assembly in a second "lower" position in which the distal end projects from the mounting surface, and a third sloping portion 148 connecting one end of the second portion with the first portion, a vertical "transition gap" being formed between the other end of the second portion and the first portion. The vertical portion 149 of the steering guide does not serve a function in this respect and may, depending on the configuration of other components of the device, being dispensed with.

To secure that the control member can only be rotated in one direction, means is provided between the control member and the non-moving members. In the shown embodiment a ratchet mechanism is formed between the control member and the core member. More specifically, the shown ratchet mechanism comprises a circumferential teethed portion 125 formed on the inner surface of the control member and an elastic arm member 144, formed on the core member, having a free end uni-directionally engaging the teeth, the control member further comprising a protrusion 126 serving as a stop for the arm member.

Shown schematically in FIG. 2, delivery means comprising a drug reservoir 105 and associated expelling means 106 is arranged inside the device and in fluid communication with the common fluid conduit 150.

Next, operation of the first embodiment will be described. On top of the device a number of positions is indicated: "Unused" in which all needles are in a retracted initial position, positions "1", "2" and "3" in which a corresponding needle is in its projecting position with the other needle being in their retracted position, as well as two "off"-positions and a single "used"-position located after the positions "1", "2" and "3" respectively.

The device is supplied to the user with the gripping member pointing on the "unused" position, i.e. with all the unused needles in their retracted position, with the steering pins supported on the upper guide surface. After the removable release liner covering the adhesive has been removed, the device has been arranged on a suitable skin portion of the user, the gripping member is turned (or "dialled") clockwise to position "1", whereby the guide surface is moved relative to the needle assemblies. Corresponding to position "1" the transition gap is moved past the first needle assembly whereby the needle assembly is "released" and biased downwardly by the associated spring until the pin rests on the lower guide surface 147 corresponding to the projecting position. As the needle assembly is forced downwardly, the pointed distal end of the needle penetrates the associated end portion 152 of the conduit member, whereby a fluid communication is established between the conduit and the interior of the needle, via the side openings, when the needle is positioned in its projecting position. As the common conduit is connected to the drug delivery means, drug can now be infused through the inserted first needle. Depending on the specific nature of the drug delivery means, infusion may start and stop automatically as needles are inserted and retracted from the common conduit (or the device is arranged on the skin surface), or it may be controlled by separate means, e.g. user actuatable means.

When after a given period it is time to exchange the first needle, the user turns the gripping member to position "2" whereby the first needle is retracted and the second needle is inserted. As appears, in performing this action, the device is moved past the first "off" position in which the first needle has been retracted, but the second needle not yet inserted. More specifically, as the control member is rotated, the sloping guide surface portion 148 is moved relative to the first needle assembly (see FIG. 4) whereby it is forced upwardly against the biasing force of the spring. Corresponding to the "off" position the first needle assembly has been moved along the slope to the upper guide surface, the second needle assembly still being positioned on the upper guide surface but just in front of the transition gap. Indeed, in this position the device may also be removed from the skin with all needles in their retracted position. As the control member then is turned fully to position "2", the second needle is inserted as described above. Correspondingly, when the gripping member is turned from position "2" to position "3", the second and third needles will be operated in the same way. When the last needle (here: the third needle) has been used, the gripping member is turned to the "used" position which internally corresponds to an "off" position with two needle assemblies located on each side of the sloping guide surface portion, however, in this position the arm member 145 abuts on the stop member 126 preventing the control member to be rotated further. After this the device is removed from the skin of the user and may be discarded.

With reference to FIGS. 6 and 7 a second embodiment of a needle device will be described. More specifically, the needle device 200 comprises a base plate member 210, a housing member 230 connected to the base plate member, and two moveable control members 240, the members in combination forming a device having a generally cylindrical configuration.

The base plate member comprises a lower surface with adhesive means 215 adapted for releasable application to the skin of a subject, an upper surface from which two control posts 212 project, each having a slotted structure 213 formed on an inner (axially facing) surface thereof, and two openings 211. The housing member is in the form of a hollow cylindrical body having two upper openings 231 as well as supporting structures 232 for "vertically" guiding the control members. The housing member is connected to the base plate member at the periphery thereof. Each control member is in the form of a downwardly open, generally cylindrical hollow body having an outer surface in sliding engagement with the housing. The upper wall portion 241 of each control member has an upper surface serving as a user actuatable press-button, and a lower surface from which a needle carrier 242 projects, a needle device 261 corresponding to the needle device of the first embodiment projecting downwardly therefrom in register with one of the openings in the base plate member. The needle carrier also comprises a control element in the form of a flexible arm member with a free end portion 243 adapted to engage the slotted structure on the corresponding control post.

Between the base plate member and the upper wall portion of each of the control members a biasing means 245 (here: a helical coil spring) is arranged providing an upwardly directed force on the control member, the control member comprising engagement means 244 cooperating with corresponding structures of the housing for positioning the control member in an upper initial position.

Between the upper surface of the base plate member and the core member a common conduit member 250 is interposed, comprising two hollow arms 251 each having a peripheral needle-penetratable, self-sealing closed end portion 252 in fluid communication with an axially arranged central portion 253 which is arranged in fluid communication with an exterior tube or hose member 254 comprising a proximal end with connector means (not shown) allowing the tube to connected in fluid communication with a fluid source, e.g. a drug delivery device. In this configuration, the device represents what is known as an "infusion set".

Each combination of a control post, a control member with its control element and an associated biasing means forms a "click" mechanism allowing the control member to be positioned and locked in a lower position with the needle arranged in fluid communication with the common conduit (as in the first embodiment) and with the distal pointed end projecting from the lower surface of the base plate member, as well as subsequently returned to the initial position when pushed down a second time, whereby the needle is withdrawn. As the mechanism as such is of a general and well known type (e.g. as used in ball pens and the like) it will not be described in greater detail.

Next, operation of the second embodiment will be described. On top of the device the two control members are indicated as "1" and "2" representing to the user actuation buttons for a first respectively a second needle.

The device is supplied to the user with both control members in their upper position. After the device has been arranged on a suitable skin portion of the user and has been connected to, for example, a drug delivery means, the user presses down one of the buttons (typically the one denoted "1") resulting in insertion of the first needle and of locking of the button in its lower position. In this way it is also indicated to the user which needle is inserted. Corresponding to the first embodiment, as the needle forced downwardly, the pointed distal end of the needle penetrates the associated end portion 252 of the conduit member, whereby a fluid communication is established between the conduit and the interior of the needle, via the side openings, when the needle is positioned in its projecting position. As the common conduit is connected to a drug delivery means, drug can now be infused through the inserted first needle.

When after a given period it is time to exchange the first needle, the user again presses down button "1" whereby it is releases and returned to its initial upper position by means of the biasing means, the first needle thereby being withdrawn. Thereafter the second needle can be inserted by pressing down button "2", this as seen in FIG. 7. When the device is to be removed, the user releases the second button whereby the second needle is withdrawn where after the device safely can be removed from the skin of the user and discarded.

As appears, the second embodiment represents a relative simple version of a needle device comprising only two needles, however, three or more needles may be provided. Further, instead of the actuation means for each of the needles operating independently of each other, they may be mechanically interconnected providing improved user friendliness and safety of use. For example, the locking means may be configured such that they can only be activated in a predetermined order and only activated once. Further, activating a subsequent needle may automatically release the previously inserted needle.

Figure 8A:
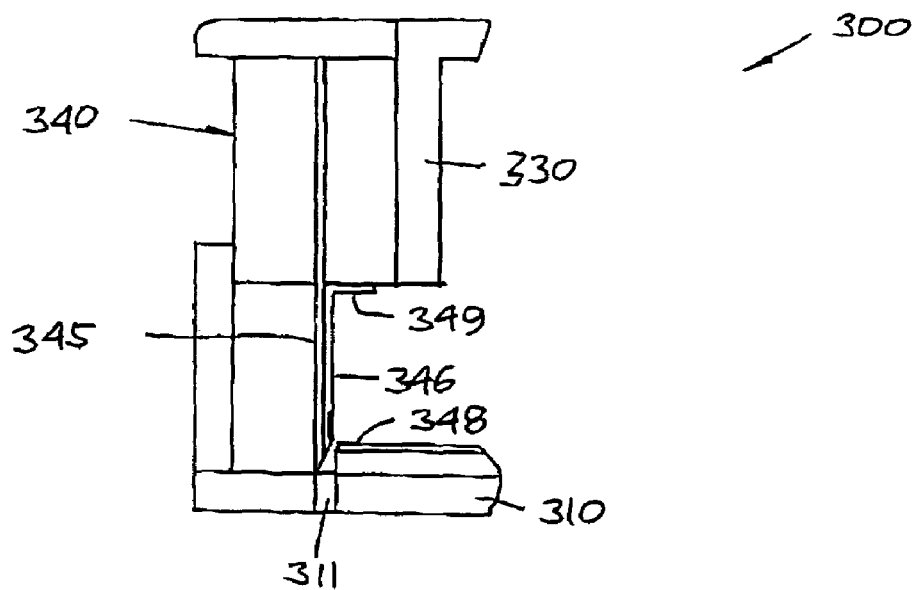
FIGS. 8A and 8B show in partial a sectional view of a further needle device.
Figure 8B:
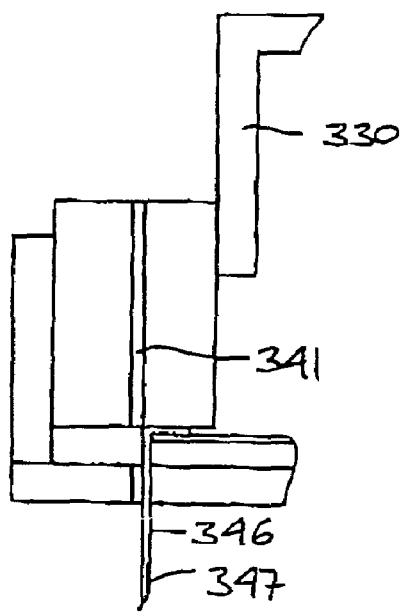

With reference to FIGS. 8A and 8B a third embodiment of a needle device will be described, having the same general configuration as the second embodiment, wherein the needle device is in the form of a combined needle sensor and corresponding insertion needle therefore, the common conduit being replaced by electrical connecting means. For improved clarity, the structures relating to the locking and release mechanism have been omitted in the drawings.

More specifically, the sensor device 300 comprises a base plate member 310 with two openings 311, a housing member 330 connected to the base plate member, and two moveable control members 340 (only one shown). The control member is provided with a bore 341 through which a relatively rigid insertion needle 345 is slidingly received, the insertion needle comprising a pointed distal end and a handle member arranged at the proximal end. Protruding downwardly from the control member is arranged a relatively flexible needle-formed sensor 346 with a distal sensor element 347 in electrical contact with proximal contact means 349, the needle-sensor being supported by the insertion needle, the support preventing deformation of the needle-sensor during insertion, yet allowing the insertion needle to be withdrawn after insertion has taken place. On the upper surface of the base plate member electrical conduit means 348 is arranged for engaging the contacts means of the sensor and conducting the received signals to signal receiving means. The signal receiving means may be contact means for connecting the sensor device to external processor means for evaluating the signals, transmitting means for wireless transmission to an external processor, or a processor arranged within the housing.

FIG. 8A shows a needle-sensor in an initial position whereas FIG. 8B shows a situation in which the needle-sensor has been inserted, contact has been established with the electrical conduit means and the insertion needle has been withdrawn.

FIGS. 9A and 9B shows a system 400 comprising sensor device 410 and an insulin delivery device 420, the delivery device comprising a first mounting surface 421 adapted for application to the skin of a subject, three infusion needles 422 each comprising a distal pointed end adapted to penetrate the skin of the subject, wherein each of the hollow needles has a first position in which the distal end is retracted relative to the first mounting surface, and a second position in which the distal end projects from the first mounting surface, the needles being arranged such that they can be moved from their first to their second position and from their second to their first position, without the other needles performing the same movement, by means of associated user actuatable needle insertion means 432. In the shown embodiment the delivery device comprises a disposable unit 423 and a durable unit 424, the disposable unit comprising the infusion needles and a drug reservoir in fluid communication with the hollow needle which is in its second position, the durable unit comprising delivery control means, expelling means for expelling a drug out of the reservoir and through the skin of the subject via the hollow needle, as well as input means 425 allowing a user to control and/or program the device, a display 426 providing the user with information, and wireless receiving means 427.

The sensor device comprises a second mounting surface 411 for application to the skin of a subject, three needle-formed sensors 412 having a distal end adapted to be inserted subcutaneously through the skin of the subject, wherein each of the needle-formed sensors has a first position in which the distal end is retracted relative to the second mounting surface, and a second position in which the distal end projects from the second mounting surface, the needle-formed sensors being arranged such that they can be moved from their first to their second position and from their second to their first position, without the other needles performing the same movement, by means of associated user actuatable needle insertion means 433, each of the needle-formed sensors being adapted for providing a sensor signal indicative of a glucose level in blood. In the shown embodiment the sensor device comprises a disposable unit 413 and a durable unit 414, the disposable unit comprising the sensor needles and the durable unit comprising sensor control means adapted to receive signals from the sensors as well as transmitting means 415. The signals are used to generate command signals in response thereto in order to keep the blood glucose level of the patient within a desired range, wherein operation of the delivery means is affected by the command signals thereby providing closed loop regulation. The command signals may be generated by the delivery control means on the basis of sensor signal received from the sensor device, or the command signals may be generated by the sensor control means directly controlling the delivery device. In an alternative embodiment, the signals are used merely to store and display information without providing closed loop regulation. In an alternative system a separate control unit is provided receiving the signals from the sensor device which then is used to control the delivery device.

FIGS. 10A and 10B shows an embodiment in which the sensor means and the drug delivery means of the above-described embodiment has been incorporated in a single disposable device 500 with a mounting surface 511 and comprising two infusion needles 522 and four sensor needles 512 in association with corresponding user actuatable needle insertion means 523, 513. The device may be provided with means for closed loop regulation of drug infusion and/or it may be provided with communication means allowing it to communicate e.g. wirelessly with separate durable control means providing user input and output means such as a display.

In the above description of the exemplary embodiments, the different structures providing mechanical and electrical contact and communication between the different components just as the means providing the described functionality for the different components (e.g. expelling means, reservoir, energy source, control means, display etc.) have been described to a degree to which the concept of the present invention will be apparent to the skilled reader. The detailed construction and specification for the different structures are considered the object of a normal design procedure performed by the skilled person along the lines set out in the present specification.

FIG. 2

Documents cited in the application and are hereby incorporated by reference.

U.S. Pat. No. 4,340,048
U.S. Pat. No. 4,552,562
U.S. Pat. No. 5,858,001
U.S. Pat. No. 6,280,148
U.S. Pat. No. 5,957,895
U.S. Pat. No. 5,527,288
EP 1 177 802
U.S. Pat. No. 4,245,634
Adam Heller, Implanted electrochemical glucose sensors for the management of diabetes, Annu. Rev. Boimed. Eng. 1999, 01:153-175
U.S. Pat. No. 5,482,473
U.S. Pat. No. 5,390,671
U.S. Pat. No. 5,391,950
U.S. Pat. No. 5,954,643
U.S. Pat. No. 5,568,806

The invention claimed is:

1. A needle device comprising:
a mounting surface adapted for application to the skin of a subject,
adhesive means arranged on the mounting surface for adhering the needle device to the skin of the subject,
a plurality of needles, each needle comprising a distal pointed end adapted to penetrate the skin of the subject, and
a common fluid conduit member having a fluid inlet adapted to receive fluid from a fluid source,
wherein each needle has a first position in which the distal end is retracted relative to the mounting surface, and a second position in which the distal end projects from the mounting surface,
wherein a plurality of the needles are hollow having a distal and a proximal opening, whereby the proximal opening of each of the hollow needles can be arranged in fluid communication with the same fluid inlet via the common fluid conduit member when the respective needle is in its second position, the proximal opening being in fluid communication with the common fluid conduit member and thereby the fluid inlet when the needle is in its second position,
wherein the needles being are arranged such that at least one needle can be moved from its first to its second position or from its second to its first position with at least one other needle not performing the same movement, and
wherein the fluid inlet is stationary relative to the mounting surface.

2. A needle device as defined in claim 1, further comprising:
needle actuating means associated with a plurality of needles, the needle actuating means being operatable between a first actuating position and a second actuating position, whereby a first associated needle is moved from its first to its second position and a second associated needle is moved from its second to its first position.

3. A needle device as defined in claim 2, wherein the needle actuating means are operatable between a plurality of actuating positions, each operation between actuating positions being associated with operation of a corresponding pair of needles between their first and second respectively second and first positions.

4. A needle device as defined in claim 2, wherein the needle actuating means is operatable between an initial position, in which all associated needles are in their first position, and an actuating position, whereby a needle is moved from its first to its second position.

5. A needle device as defined in claim 2, wherein the needle actuating means is operatable between an actuating position, in which an associated needle is in its second position, and an end position in which all associated needles are in their first position.

6. A needle device as defined in claim 2, wherein each of the associated needles are connected to a needle carrier, the actuation means comprising moveable control means in engagement with or operatable to come into engagement with the needle carriers, the position of the control means controlling operation of the needles between their respective first and/or second positions.

7. A needle device as defined in claim 6, wherein the needle carriers are associated with biasing means for moving the respective needle from its first to its second position by a force generated by the biasing means, release of the biasing means being controlled by movement of the control means.

8. A needle device as defined in claim 7, wherein the control means comprises a cam surface with a sloped portion, whereby movement of the sloped portion causes a needle to be moved from its second to its first position against the force of the biasing means.

9. A needle device as defined in claim 1, wherein at least one needle is associated with actuation means (240) comprising a biasing means (245) and being operatable between an initial position and an actuating position, whereby the needle is moved from its first to its second position against a force generated by the first biasing means.

10. A needle device as defined in claim 9, wherein the actuation means is operatable between the actuating position and an end position, whereby the needle is moved from its second to its first position by a force generated by the biasing means.

11. A needle device as defined in any of claims 2-10, further comprising electronically controllable driving means for operating the needle actuating means between at least two actuating positions.

12. A needle device as defined in claim 2, further comprising means preventing a needle from being moved from its first to its second position more than once.

13. A needle device as defined in claim 1, wherein the proximal opening of a hollow needle is not in fluid communication with the common fluid conduit means when the needle is in its first position.

14. A needle device as defined in claim 1, further comprising:
a reservoir adapted to contain a liquid drug and comprising an outlet in fluid communication with the common fluid conduit means.

15. A needle device as defined in claim 14, further comprising:
expelling means for expelling a drug out of the reservoir and through the skin of the subject via the common fluid conduit means and a hollow needle.

16. A needle device as defined in claim 13, wherein the common fluid conduit means comprises a fluid inlet means.

17. A needle device as defined in claim 13, further comprising means for withdrawing a body fluid through at least one of the hollow needles, the needle device preferably comprising sensor means capable of being influenced by a body substance drawn through the needle and producing a signal corresponding thereto.

18. A needle device as defined in claim 1, wherein at least one of the needles is in the form of a needle sensor comprising sensor means capable of being influenced by a body substance and producing a signal corresponding thereto.

19. A needle device as defined in claim 18, further comprising an insertion needle adapted to cooperate with a corresponding needle sensor for inserting the needle sensor subcutaneously.

20. A needle device as defined in claim 1, wherein the plurality of needles comprises at least two hollow infusion needles, the hollow infusion needles being arranged such that only one infusion needle can be positioned in the second position at a given time.

21. A needle device as defined in claim 1, further comprising a delivery means in fluid communication with the common fluid member, the delivery means comprising a drug reservoir and associated expelling means arranged inside the device.

22. A needle device as defined in claim 1, further comprising an exterior tube or hose member in fluid communication with the common fluid member, the exterior tube or hose member being adapted to be connected to an external fluid source.

23. A needle device as in claim 1, wherein the needles are arranged non-rotationally relative to the mounting surface.

* * * * *